United States Patent
Taylor et al.

(10) Patent No.: US 9,202,010 B2
(45) Date of Patent: *Dec. 1, 2015

(54) SYSTEMS AND METHODS FOR MODELING CHANGES IN PATIENT-SPECIFIC BLOOD VESSEL GEOMETRY AND BOUNDARY CONDITIONS

(71) Applicant: HeartFlow, Inc., Redwood City, CA (US)

(72) Inventors: Charles A. Taylor, San Mateo, CA (US); Hyun Jin Kim, San Mateo, CA (US); Sethuraman Sankaran, Palo Alto, CA (US); Michiel Schaap, Mountain View, CA (US); David Eberle, San Francisco, CA (US); Gilwoo Choi, Mountain View, CA (US); Leo Grady, Millbrae, CA (US)

(73) Assignee: HeartFlow, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/323,201

(22) Filed: Jul. 3, 2014

(65) Prior Publication Data

US 2015/0269352 A1  Sep. 24, 2015

Related U.S. Application Data

(63) Continuation of application No. 14/317,726, filed on Jun. 27, 2014.

(60) Provisional application No. 61/969,573, filed on Mar. 24, 2014.

(51) Int. Cl.
*G06F 19/00* (2011.01)

(52) U.S. Cl.
CPC .................................. *G06F 19/3437* (2013.01)

(58) Field of Classification Search
None
See application file for complete search history.

(56) References Cited

U.S. PATENT DOCUMENTS

| | | |
|---|---|---|
| 8,249,815 B2 | 8/2012 | Taylor |
| 8,315,812 B2 | 11/2012 | Taylor |
| 2010/0017171 A1 | 1/2010 | Spilker et al. |
| 2012/0041320 A1 | 2/2012 | Taylor |
| 2012/0041739 A1* | 2/2012 | Taylor ............................. 703/11 |
| 2012/0053918 A1 | 3/2012 | Taylor |
| 2012/0084064 A1 | 4/2012 | Dzenis et al. |
| 2012/0232386 A1* | 9/2012 | Mansi et al. .................. 600/437 |

FOREIGN PATENT DOCUMENTS

WO  WO 2013/071219 A1  5/2013

OTHER PUBLICATIONS

Abbara S, Arbab-Zadeh A, Callister TQ, et al. SCCT guidelines for performance of coronary computed tomographic angiography: a report of the Society of Cardiovascular Computed Tomography Guidelines Committee. J Cardiovasc Comput Tomogr 2009;3:190-204.).
In Olufsen et al. (Olufsen MS. Structured tree outflow condition for blood flow in larger systemic arteries. Am J Physiol Heart Circ Physiol 276:H257-H268, 1999).
Wan et al. (J. Wan, B.N. Steele, S.A. Spicer, S. Strohband, G.R. Feijoo, T.J.R. Hughes, C.A. Taylor (2002) A One-dimensional Finite Element Method for Simulation-Based Medical Planning for Cardiovascular Disease. Computer Methods in Biomechanics and Biomedical Engineering. vol. 5, No. 3, pp. 195-206.).
Raghu et al. (R. Raghu, I.E. Vignon-Clementel, C.A. Figueroa, C.A. Taylor (2011) Comparative Study of Viscoelastic Arterial Wall Models in Nonlinear One-dimensional Finite Element Simulations of Blood Flow. Journal of Biomechanical Engineering, vol. 133, No. 8, pp. 081003.).
In Figueroa et al. (C.A. Figueroa, I.E. Vignon-Clementel, K.C. Jansen, T.J.R. Hughes, C.A. Taylor (2006) A Coupled Momentum Method for Modeling Blood Flow in Three-Dimensional Deformable Arteries. Computer Methods in Applied Mechanics and Engineering, vol. 195, Issues 41-43, pp. 5685-5706.).
Figueroa et al. (C.A. Figueroa, S. Baek, C.A. Taylor, J.D. Humphrey (2009) A Computational Framework for Coupled Fluid-Solid Growth Modeling in Cardiovascular Simulations. Computer Methods in Applied Mechanics and Engineering, vol. 198, No. 45-46, pp. 3583-3602.).
Gee et al (Gee MW, Förster C, Wall WA (2010) A computational strategy for prestressing patient-specific biomechanical problems under finite deformation. Int J Numer Methods Biomed Eng 26(1):52-72).
Gerbeau et al. (Gerbeau J-F, Vidrascu M, Frey P (2005) Fluid-structure interaction in blood flows on geometries based on medical imaging. Comput Struct 83(2-3):155-165).
Kioussis et al (Kiousis DE, Gasser TC, Holzapfel GA. 2007. A numerical model to study the interaction of vascular stents with human atherosclerotic lesions. Ann. Biomed. Eng. 35:1857-69).
International Search Report and Written Opinion for corresponding Application No. PCT/US2015/022062 dated Jul. 2, 2015 (9 pages).
Taylor et al. (inventor): *Patient-Specific Modeling of Cardiovascular Mechanics*; Ann. Rev. Biomed. Eng. 2009. 11:109-136.
Spilker and Taylor (inventor): *Tuning Multidomain Hemodynamic simulations to Match Physiological Measurement*; Annals of Biomedical Engineering, vol. 38, No. 8, Aug. 2010 (2010) pp. 2635-2648.

(Continued)

*Primary Examiner* — Lori A. Clow
(74) *Attorney, Agent, or Firm* — Bookoff McAndrews, PLLC (57) ABSTRACT

Systems and methods are disclosed for modeling changes in patient-specific blood vessel geometry and boundary conditions resulting from changes in blood flow or pressure. One method includes determining, using a processor, a first anatomic model of one or more blood vessels of a patient; determining a biomechanical model of the one or more blood vessels based on at least the first anatomic model; determining one or more parameters associated with a physiological state of the patient; and creating a second anatomic model based on the biomechanical model and the one or more parameters associated with the physiological state.

24 Claims, 5 Drawing Sheets

(56) References Cited

OTHER PUBLICATIONS

Chabiniok et al.: *Validation of a biomechanical heart model using animal data with acute myocardial infarction*; CI2BM09—MICCAI Workshop on Cardiovascular Interventional Imaging and Biophysical Modeling; 2009; 9 pages.

Moireau et al.: *Cardiac Motion Extraction From Images by Filtering Estimation Based on a Biomechanical Model*; FIMH 2009, LNCS 5528; Springer-Verlag; 2009; pp. 220-228.

Marchesseau et al.: *Cardiac Mechanical Parameter Calibration Based on the Unscented Transform*; N. Ayache et al. (Eds.): MICCAI 2012, Part II, LNCS 7511, Springer-Verlag; pp. 41-48, 2012; pp. 41-48.

Stergiou et al.: *Baseline Measures are Altered in Biomechanical Studies*; Journal of Biomechanics 38 (2005) 175-178.

Mann et al.: Mechanisms and Models in Heart Failure: *The Biomechanical Model and Beyond; Circulation;* (published by the American Heart Association); 2005; pp. 2837-2849 914 pages total).

Tang et al. (and inventor): *Abdominal Aortic Hemodynamics in Young Healthy Adults at rest and during lower limb exercise: quantification using image-based computer modeling*; Am J. Phsiol Heart Circ. Physiol 291: H668-H676, 2006.

Fridez et al.: *Model of Geometrical and Smooth Muscle Tone Adaptation of Carotid Artery Subject to Step change in Pressure*; Am J Physiol Heart Circ Physiol; 280: H2752-2760, 2001.

Larrabide et al.: *GIMIAS: An Open Source Framework for Efficient Development of Research Tools and Clinical Prototypes*; FIMH 2009, LNCS 5528; Springer-Verlag; pp. 417-426, 2009.

Sermesant et al.: *Biomechanical Model Construction from Different Modalities: Application to Cardiac Images*; LNCS 2488; Springer-Verlag; pp. 714-721, 2002.

Marchesseau and Delingette et al.: *Fast Parameter Calibration of a Cardiac Electromechanical Model From Medical Images Based on the Unscented Transform*; Biomech Model Mechanobiol (2013) 12:815-831.

Sermesant et al.: *Personalized Computational Models of the Heart for Cardiac Resynchronization Therapy*; Chapter 10, *Patient-Specific Modeling of the Cardiovascular System: Technology-Driven Personalized Medicine*; 2010; pp. 167-182.

Alexandra Bugalho de Moura; *The Geometrical Multiscale Model of the Cardiovascular System: Coupling 3D FSI and 1D Models*; presente to Dipartimento di Matematica "F. Brioschi" Politecnico Di Milano, matricola: D02009, 2007-PhD Thesis.

Andro Mikelic et al.: *Fluid-Structure Interaction in Blood Flow, MSRI; The Legacy of Ladyzhenskaya and Oleinik: Women in Mathematics*: May 18-20, (2006), pp. 11-16.

Suncica Canic, et al. *Self-Consistent Effective Equations Modeling Blood Flow in Medium-To-Large Compliant Arteries*: Fluid Structure-Interaction in Hemodynamics, pp. 1-38, 2005.

Emilie Marchandise et al.; *A Numerical Hemodynamic Tool for Predictive Vascular Surgery*, Oct. 5, 2007, Medical Engineering & Physics, pp. 1-21.

Daniela Valdez-Jasso; *Linear and Nonlinear Viscoelastic Modeling of Aorta and Carotid Pressure-Area Dynamics under in vivo and ex vivo Conditions*; Published in final edited from as: Ann Biomed. Eng. May 2011; 39(5): 1438-1456.

Canic et al. (SIAM J. Multisci. Anal. Simul. 3(3) :559-596 (2005).

\* cited by examiner

SYSTEMS AND METHODS FOR MODELING CHANGES IN PATIENT-SPECIFIC BLOOD VESSEL GEOMETRY AND BOUNDARY CONDITIONS

RELATED APPLICATION(S)

This application is a continuation of pending U.S. application Ser. No. 14/317,726, filed Jun. 27, 2014, which claims priority to U.S. Provisional Application No. 61/969,573 filed Mar. 24, 2014, the entire disclosures of which are hereby incorporated by reference in their entirety.

FIELD OF THE INVENTION

Various embodiments of the present disclosure relate generally to medical modeling and related methods. More specifically, particular embodiments of the present disclosure relate to systems and methods for modeling changes in patient-specific blood vessel geometry and boundary conditions resulting from changes in blood flow or pressure.

BACKGROUND

Coronary artery disease may cause the blood vessels providing blood to the heart to develop lesions, such as a stenosis (abnormal narrowing of a blood vessel). As a result, blood flow to the heart may be restricted. A patient suffering from coronary artery disease may experience chest pain, referred to as chronic stable angina during physical exertion or unstable angina when the patient is at rest. A more severe manifestation of disease may lead to myocardial infarction, or heart attack.

A need exists to provide more accurate data relating to coronary lesions, e.g., size, shape, location, functional significance (e.g., whether the lesion impacts blood flow), etc. Patients suffering from chest pain and/or exhibiting symptoms of coronary artery disease may be subjected to one or more tests that may provide some indirect evidence relating to coronary lesions. For example, noninvasive tests may include electrocardiograms, biomarker evaluation from blood tests, treadmill tests, echocardiography, single positron emission computed tomography (SPECT), and positron emission tomography (PET). These noninvasive tests, however, typically do not provide a direct assessment of coronary lesions or assess blood flow rates. The noninvasive tests may provide indirect evidence of coronary lesions by looking for changes in electrical activity of the heart (e.g., using electrocardiography (ECG)), motion of the myocardium (e.g., using stress echocardiography), perfusion of the myocardium (e.g., using PET or SPECT), or metabolic changes (e.g., using biomarkers).

For example, anatomic data may be obtained noninvasively using coronary computed tomographic angiography (CCTA). CCTA may be used for imaging of patients with chest pain and involves using computed tomography (CT) technology to image the heart and the coronary arteries following an intravenous infusion of a contrast agent. However, obtaining anatomic data using CCTA often means that models based on the anatomic data reflect a patient's state as he/she is undergoing imaging (e.g., CCTA imaging). Therefore, anatomic models for assessing blood flow rates are based on patient conditions during an imaging procedure. For example, patient-specific anatomic models for simulating arterial blood flow are often obtained while a patient is in a baseline condition during imaging and prior to treatment. However, various forms of treatment may affect anatomy and consequently, blood flow. In other words, a patient's state may change due to any array of medical procedures and/or health conditions. Meanwhile, models for assessing blood flow may fail to reflect the change in state. As a result, there is a need for methods and systems accounting for changes in a patient's physiological state in indirect assessments of blood flow rates. In particular, there is a need for methods and systems for creating an anatomical model based on a patient's change in state in order to improve the accuracy of a simulation performed using the model. More specifically, creating an anatomical model may entail modeling changes in patient-specific blood vessel geometry and boundary conditions.

The foregoing general description and the following detailed description are exemplary and explanatory only and are not restrictive of the disclosure.

SUMMARY

According to certain aspects of the present disclosure, systems and methods are disclosed for anatomical modeling. One method includes: determining, using a processor, a first anatomic model of one or more blood vessels of a patient; determining a biomechanical model of the one or more blood vessels based on at least the first anatomic model; determining one or more parameters associated with a physiological state of the patient; and creating a second anatomic model based on the biomechanical model and the one or more parameters associated with the physiological state.

In accordance with another embodiment, a system for anatomical modeling comprises: a data storage device storing instructions for anatomical modeling; and a processor configured for: determining, using a processor, a first anatomic model of one or more blood vessels of a patient; determining a biomechanical model of the one or more blood vessels based on at least the first anatomic model; determining one or more parameters associated with a physiological state of the patient; and creating a second anatomic model based on the biomechanical model and the one or more parameters associated with the physiological state.

In accordance with yet another embodiment, a non-transitory computer readable medium for use on a computer system containing computer-executable programming instructions for anatomical modeling is provided. The method includes: determining, using a processor, a first anatomic model of one or more blood vessels of a patient; determining a biomechanical model of the one or more blood vessels based on at least the first anatomic model; determining one or more parameters associated with a physiological state of the patient; and creating a second anatomic model based on the biomechanical model and the one or more parameters associated with the physiological state.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

Often, patient-specific anatomic models for simulating arterial blood flow are based on image data associated with one state. In one example, coronary artery anatomic data may be obtained under baseline or resting conditions. In another example, coronary artery anatomic data may be obtained based on an anatomic state achieved during imaging, including states that increase blood vessel size and blood flow to improve image quality. Geometric models may be created and boundary conditions assigned based on the image data from a baseline condition or imaging conditions. Simulations modeling reversible, physiological states (e.g., blood flow simulations associated with drugs, exercise, and/or treatment) are often performed based on the anatomic and geometric model associated with the first state. However, drugs, exercise, and/or treatment may all cause changes in blood vessel geometry and boundary conditions from the first state. For example, a geometry of a patient's anatomy may change due to various conditions or treatments, including administration of drugs (e.g., adenosine or other drugs to increase blood flow), simulations of medical conditions (e.g., simulated hyperemia), simulations of physical activities or conditions (e.g., exercise), angioplasty, surgery (e.g., stenting or bypass grafting), etc. Therefore, a desire exists for patient-specific models for simulating arterial blood flow that may account for a representation of a patient's state, where the patient's state may differ from a state from which the anatomic model was built. Simulating arterial blood flow using a patient-specific model reflecting a second state may improve accuracy of simulation results. Particularly, the present disclosure is directed to second state(s) that may include reversible, physiological states. Furthermore, simulations and models based on the second state may further be applied to model possible treatments that may affect geometry (e.g., angioplasty, stenting, and/or bypass surgery). For example, a geometric change to a model may be made (e.g., to model stenting), based on patient-specific models that reflect a second state. The following discussion outlines various scenarios where an anatomic and biomechanical model under which simulations are performed, may not accurately represent a patient's state.

In one embodiment, simulations may be performed using patient-specific anatomic models based on image data obtained under resting conditions. Geometric models and boundary condition models based on these baseline conditions may then be used as input to computer models in order to predict flow and pressure under a physiologic state, including during the administration of adenosine or other drugs to increase blood flow and simulate exercise, or after angioplasty and stenting or bypass grafting. The patient's anatomy may be at a state distinct from the first, resting state, in light of one or more treatments or conditions. Therefore, a desire exists for patient-specific models for simulating arterial blood flow to take into account a second state reflecting patient anatomy at a non-resting state.

In another embodiment, a patient-specific model extracted from image data may be based on a state distinct from a baseline state. For instance, in the case of coronary artery anatomic data, beta blockers may be used to reduce heart rate, while nitrates may be administered to dilate large coronary arteries. Both drugs may be administered to improve image quality. For example, beta blockers used to slow the heart may affect blood pressure and hence, the size of a vessel; and nitrates used during coronary computed tomography (CT) angiography may increase flow by relaxing smooth muscle cells in blood vessels, decreasing their tension (or tone), and increasing the size of the blood vessels. The increased size and flow through the vessels improves image quality. The administration of beta blockers and/or nitrates may cause geometry and physiologic conditions to change to a state that may be different from a baseline state. However, the new state of the arteries from the administration of beta blockers and/or nitrates changes geometry and physiologic conditions to a state that may be different from a baseline. In other words, modeled changes in blood flow and pressure may cause changes in patient-specific geometric models and boundary conditions, since local vessel size may be affected by local pressure and smooth muscle tone of the vessels (which can be affected by administration of nitrates, adenosine, papaverine, adenosine triphosphate (ATP), etc.). However, an image created from baseline conditions may not account for the affect that drugs may have on anatomy geometry and boundary conditions. A blood flow simulation performed under the state may be expected to yield diagnostic data different from that attained prior to the administration of the drugs. Thus, the present disclosure is directed to a new approach including changing geometry and boundary conditions in a blood flow simulation to model an original baseline or resting state of arteries prior to administration of drugs.

A specific example of the above embodiment may include modeling of increased flow as occurs during simulated hyperemia. Such modeling may be performed to calculated fractional flow reserve or coronary flow reserve. The simulations of increased flow may be typically performed based on coronary anatomic data obtained under baseline or resting conditions. In reality, the data is often obtained subsequent to administration of beta blockers and/or nitrates. More specifically, simulation of increased blood flow through coronary arteries may result in pressure changes along the coronary arteries, especially downstream of a coronary artery stenosis. The metric of FFR may be calculated from the ratio of downstream pressure to aortic pressure. As a result during the simulation of hyperemia (performed using anatomic data obtained at baseline), blood pressure may be significantly lower at points downstream of the vessel rather than at points upstream of the vessel. Also, blood pressure may be significantly lower during the hyperemic state than during the resting state. The blood vessels may diminish in size (i.e., "deflate") due to the reduced pressure. Such changes in vessel size may affect tightness of a coronary artery stenosis or the caliber of vessels downstream from the stenosis. This in turn may affect the accuracy of the hyperemic simulation and accuracy of the predicted FFR, as compared to measured data (obtained during actual administration of vasodilators causing increased flow and pressure reduction along the length of the vessel). Thus, the present disclosure is directed to a new approach for changing geometry and boundary conditions in a blood flow simulation model of the hyperemic state of arteries using image data obtained without administration of drugs to increase blood flow.

Furthermore, treatment recommendations may be improved with modeling taking into account changes in patient-specific blood vessel geometry and boundary conditions. For example, percutaneous coronary intervention (PCI) or coronary artery bypass grafting (CABG) is often used to treat patients with coronary artery disease. Computer models are often used to predict changes in blood flow or pressure resulting from the treatments to aid the physician in deciding how best to treat a given patient. Patient-specific models for simulating PCI or CABG may be created from pre-treatment image data, then modified to incorporate a treatment plan. The modifications are generally restricted to geometric changes in diseased segments to account for dilation of stenosis with PCI or creation of an alternate conduit for blood flow with CABG.

However, treatments may affect more than simply diseased segments. Treatments potentially change blood flow and pressure in an entire coronary artery tree. Therefore, the present disclosure is further directed to a new approach for modeling geometric changes and boundary condition changes secondary to changes in blood flow or pressure resulting from treatments for arterial disease. For example, the present disclosure may include updating geometric model and boundary conditions (created from pre-treatment data) to account for new post-treatment flow and pressure. In other words, the present disclosure may include changing geometry and boundary conditions in a blood flow simulation to model post-treatment state of arteries due to predicted changes in blood flow and pressure from models originally created using image data obtained prior to treatment.

In a broader sense, the present disclosure is directed to a new approach for systems and methods for modeling changes in patient-specific blood vessel geometry and boundary conditions based on changes in blood flow or pressure.

Figure 1:
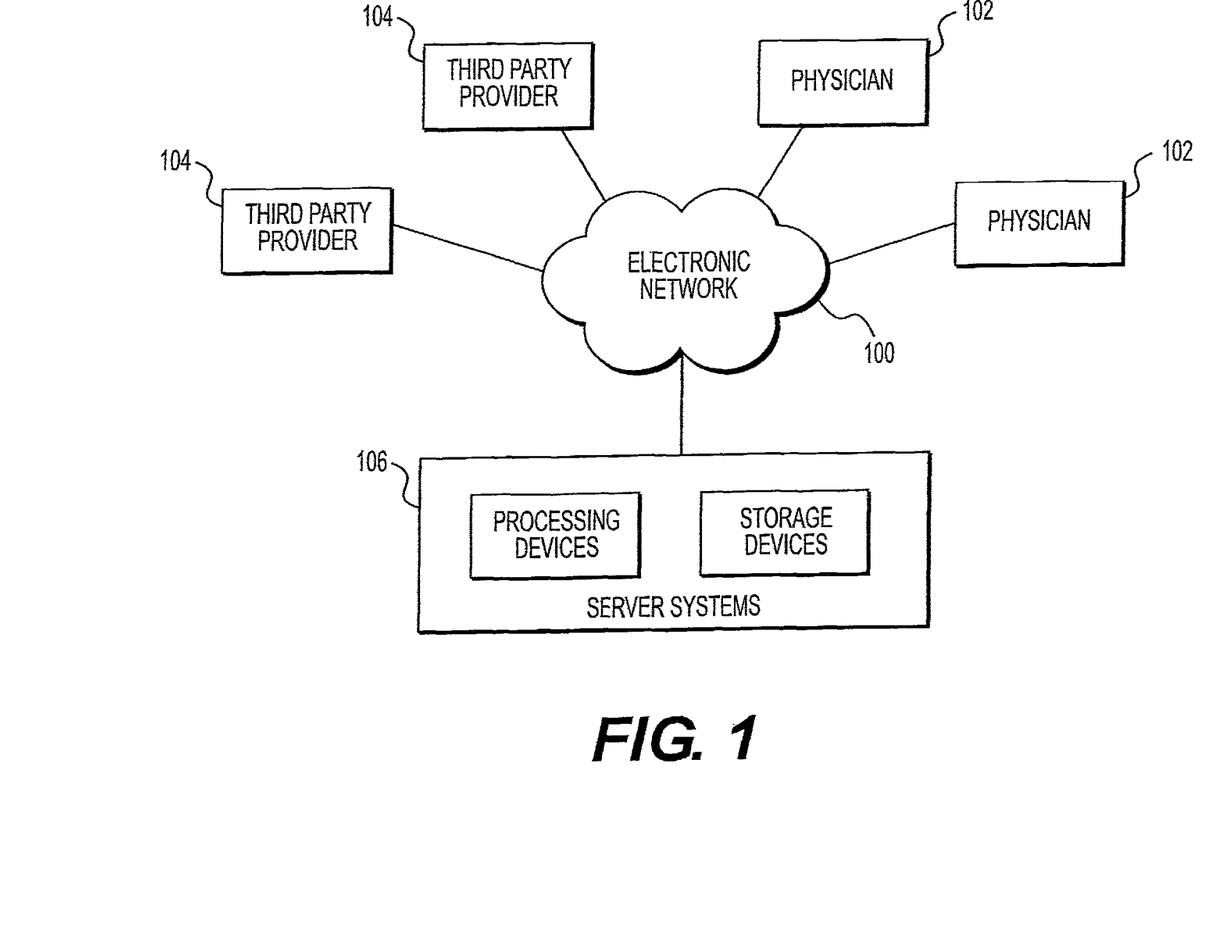
FIG. 1 is a block diagram of an exemplary system and network for modeling changes in patient-specific blood vessel geometry and boundary conditions, according to an exemplary embodiment of the present disclosure.

Referring now to the figures, FIG. 1 depicts a block diagram of an exemplary system and network for modeling changes in patient-specific blood vessel geometry and boundary conditions. Specifically, FIG. 1 depicts a plurality of physicians 102 and third party providers 104, any of whom may be connected to an electronic network 100, such as the Internet, through one or more computers, servers, and/or handheld mobile devices. Physicians 102 and/or third party providers 104 may create or otherwise obtain images of one or more patients' cardiac and/or vascular systems. The physicians 102 and/or third party providers 104 may also obtain any combination of patient-specific information, such as age, medical history, blood pressure, blood viscosity, etc. Physicians 102 and/or third party providers 104 may transmit the cardiac/vascular images and/or patient-specific information to server systems 106 over the electronic network 100. Server systems 106 may include storage devices for storing images and data received from physicians 102 and/or third party providers 104. Server systems 106 may also include processing devices for processing images and data stored in the storage devices.

Figure 2:
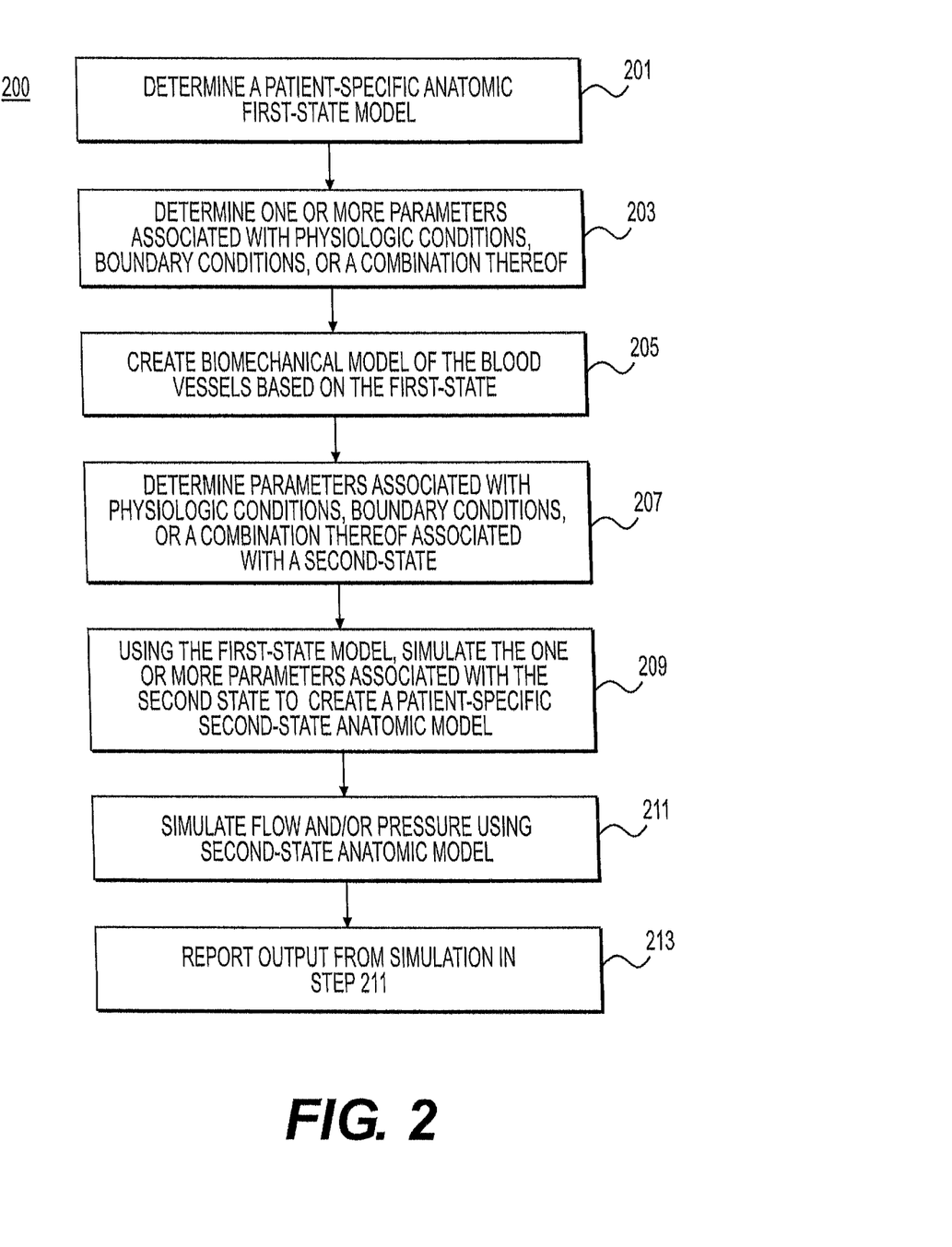
FIG. 2 is a block diagram of an exemplary method of changing geometry and boundary conditions in a blood flow simulation arising from different states of a patient, according to an exemplary embodiment of the present disclosure.

FIG. 2 is a block diagram of an exemplary method 200 of changing geometry and boundary conditions in a blood flow simulation to model a second state of a patient different from a first state of the patient (e.g., from the state in which the patient was imaged), according to an exemplary embodiment. The second state, for example, may be (1) a resting state, free of the administration of drugs used during imaging, (2) a hyperemic state of arteries, free of drugs used to increase blood flow, (3) a post-treatment state, or (4) any other desired state.

In one embodiment, step 201 may include constructing a patient-specific anatomic model. In one embodiment, the model may be from two-dimensional imaging modalities (e.g., coronary angiography, biplane angiography, etc.) or three-dimensional imaging modalities (e.g., 3-D rotational angiography, coronary computed tomographic angiograph (cCTA), magnetic resonance angiography (MRA)). Step 201 may further include directly segmenting image data and creating a patient-specific three-dimensional anatomic model of the patient's arteries. Alternately or in addition, step 201 may involve modifying a previously-constructed "generic" model, customizing the model for a particular patient, and creating a patient-specific model. In yet another embodiment, step 201 may include providing, receiving, and/or loading a patient-specific anatomic model of a patient into a computer. For example, the model may be from an electronic storage device (e.g., a hard drive, network drive, etc.). In one embodiment, the model may represent a first, baseline state of a patient.

In any or all of the embodiments of step 201, the patient-specific anatomic model may include information related to arteries of interest, including the length of each segment, diameter along the length of a segment (or any other geometric description of the segment), branching patterns, presence of disease, characteristics of disease (including composition of atherosclerotic plaques), etc. A representation of the patient-specific model may be defined by a surface enclosing a three-dimensional volume, a one-dimensional model where the centerline of the vessels is defined together with cross-sectional area information along the length, and/or an implicit representation of a vessel surface.

In one embodiment, step 203 may include defining physiologic conditions associated with blood flow and pressure that reflect a patient's condition at the time that imaging was taken. Conditions at the time of imaging may make up a "first (physiological) state" for a patient. For example, a patient may be administered beta blockers to lower his heart rate and/or sublingual nitrates to dilate his coronary arteries in order to improve image quality. Step 203 of determining physiologic conditions may include determining and/or assigning aortic pressure conditions and resistance of coronary artery microcirculation based on a patient's intake of beta blockers and/or nitrates.

In one embodiment, step 205 may include creating a biomechanical model of a vessel wall, for example, generating a biomechanical model for each segment of artery extracted in the patient-specific anatomic model of step 201. In one embodiment, the vessel wall model may be based on one-dimensional elastic or viscoelastic models of blood vessels. Such models may include models that typically relate pressure to vessel cross-sectional area along the length of a vessel. Exemplary models are described in Olufsen et al. (Olufsen M S. "Structured tree outflow condition for blood flow in larger systemic arteries." Am J Physiol Heart Circ Physiol 276:

H257-H268, 1999.), Wan et al. (J. Wan, B. N. Steele, S. A. Spicer, S. Strohband, G. R. Feijoo, T. J. R. Hughes, C. A. Taylor (2002) "A One-dimensional Finite Element Method for Simulation-Based Medical Planning for Cardiovascular Disease." Computer Methods in Biomechanics and Biomedical Engineering. Vol. 5, No. 3, pp. 195-206.), and Raghu et al. (R. Raghu, I. E. Vignon-Clementel, C. A. Figueroa, C. A. Taylor (2011) "Comparative Study of Viscoelastic Arterial Wall Models in Nonlinear One-dimensional Finite Element Simulations of Blood Flow." Journal of Biomechanical Engineering, Vol. 133, No. 8, pp 081003.). Alternately, biomechanical models of vessel wall may represent the vessel wall as a surface with spatially-varying thickness and material properties, for example, as described in Figueroa et al. (C. A. Figueroa, I. E. Vignon-Clementel, K. C. Jansen, T. J. R. Hughes, C. A. Taylor (2006) "A Coupled Momentum Method For Modeling Blood Flow In Three-Dimensional Deformable Arteries." Computer Methods in Applied Mechanics and Engineering, Vol. 195, Issues 41-43, pp. 5685-5706.) or in Figueroa et al. (C. A. Figueroa, S. Baek, C. A. Taylor, J. D. Humphrey (2009) "A Computational Framework for Coupled Fluid-Solid Growth Modeling in Cardiovascular Simulations." Computer Methods in Applied Mechanics and Engineering, Vol. 198, No. 45-46, pp. 3583-3602.). Another example of a biomechanical model may include a blood vessel as a three-dimensional continuum model, as in Gee et al. (Gee M W, Forster C, Wall W A (2010) "A computational strategy for prestressing patient-specific biomechanical problems under finite deformation." Int J Numer Methods Biomed Eng 26(1):52-72.), Gerbeau et al. (Gerbeau J-F, Vidrascu M, Frey P (2005) "Fluid-structure interaction in blood flows on geometries based on medical imaging." Comput Struct 83(2-3):155-165.), or as in Kioussis et al. (Kiousis D E, Gasser T C, Holzapfel G A. 2007. A numerical model to study the interaction of vascular stents with human atherosclerotic lesions. Ann. Biomed. Eng. 35:1857-69.). Material properties of vessel walls may be defined based on population averaged material properties, imaging data, and/or data inferred by experimental measurement of deformation of coronary arteries during a cardiac cycle and solving an inverse optimization problem to estimate the best constitutive fit consistent with data. Examples of constitutive models include linear elastic, hyperelastic, linear and nonlinear viscoelastic models including those discussed in Wan et al. (J. Wan, B. N. Steele, S. A. Spicer, S. Strohband, G. R. Feijoo, T. J. R. Hughes, C. A. Taylor (2002) A One-dimensional Finite Element Method for Simulation-Based Medical Planning for Cardiovascular Disease. Computer Methods in Biomechanics and Biomedical Engineering. Vol. 5, No. 3, pp. 195-206), Raghu et al. ([R. Raghu, I. E.]Vignon-Clementel, C. A. Figueroa, C. A. Taylor (2011) Comparative Study of Viscoelastic Arterial Wall Models in Nonlinear One-dimensional Finite Element Simulations of Blood Flow. Journal of Biomechanical Engineering, Vol. 133, No. 8, pp 081003.) and Taylor et al. (C. A. Taylor, J. D. Humphrey (2009) Open Problems in Computational Vascular Biomechanics: Hemodynamics and Arterial Wall Mechanics. Computer Methods in Applied Mechanics and Engineering, 198, No. 45-46, pp. 3514-3523). These material models may be purely phenomenological stress-strain relations or phenomenological models that are based on the microstructure of blood vessels, e.g. including data on collagen and elastin fiber orientation derived from experimental data, see for example Humphrey et al. (J. D. Humphrey, Cardiovascular Solid Mechanics: Cells, Tissues, and Organs, Springer, New York, 2002.) and Holzapfel et al. (G. A. Holzapfel, T. C. Gasser, R. W. Ogden, A new constitutive framework for arterial wall mechanics and a comparative study of material models, J. Elasticity (2000) 1-48).

In one embodiment, an elastic modulus of a vessel wall may be roughly estimated from a Hounsfield unit (HU) of tissue surrounding a lumen boundary. Thickness of a vessel wall may be estimated from image data and/or approximated by a theoretical relationship between vessel radius and wall thickness, e.g., assuming the thickness is $\frac{1}{5}^{th}$ or $\frac{1}{10}^{th}$ of the radius. Vessel wall models may represent material behavior passively or may include active behavior to model tension due to smooth muscle tone in the vessel wall. The material properties may be affected by pressure, flow, wall shear stress, wall tensile stress, and/or vasoactive drugs that may alter tension in the vessel wall (e.g., by inducing smooth muscle cell contraction or relaxation).

In one embodiment, steps 201-205 of determining a patient-specific geometrical model, a physiologic model, and a biomechanical model may all pertain to a "first state." In some embodiments, such a first-state model may represent the patient's conditions when imaging was performed.

Figure 5:
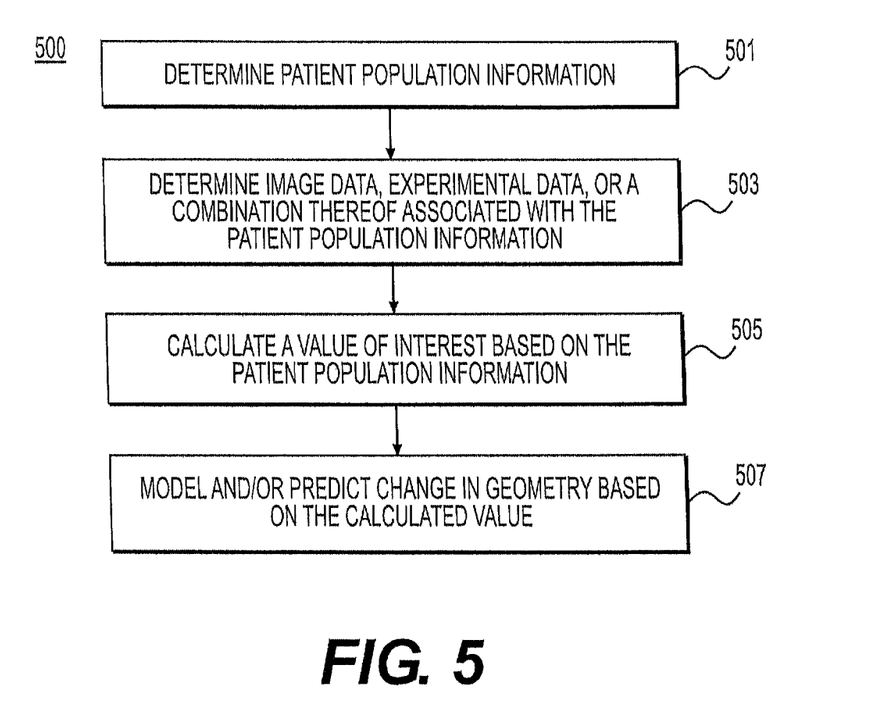
FIG. 5 is a block diagram of an exemplary method of determining geometry responses to different physiologic conditions, according to an exemplary embodiment of the present disclosure.

In one embodiment, step 207 may include defining physiologic conditions, boundary conditions, and/or material properties of a patient in a second state, other than the first state. For example, physiologic conditions and boundary conditions of a patient under hyperemic conditions may be defined using a method described in U.S. Pat. No. 8,315,812 issued Nov. 20, 2012, the entire disclosure of which is hereby incorporated by reference in its entirety. The physiologic conditions and boundary conditions of a patient after treatment may be defined using the method described in U.S. Pat. No. 8,249,815 issued Aug. 21, 2012, the entire disclosure of which is hereby incorporated in reference in its entirety. In one embodiment, changes in elastic properties of a blood vessel may be modified for a second state based on an expected response to medications (e.g., nitrates). For example, if nitrates were used during imaging of a patient, a second state may include determining vasoactive response of arteries in response to a "removal" of nitrates. The second state may thus include vasoconstriction of arteries relative to the first state, which may closer model a patient's anatomy and/or physiology under resting conditions. In some embodiments, step 207 may include determining changes in properties based on data in literature. For example, an expected response of nitrates known in literature, is an increase in diameters of 0% to 30%, depending on the size of a vessel and whether it is healthy or diseased. In another embodiment, if image data is available for a population of patients with and without nitrates, changes in vessel size due to administration of nitrates may be determined using machine learning methods. The data may then be used to update vessel properties for the second state of the patient. FIG. 5, described further herein, provides further detail on machine learning methods for determining changes in geometry with respect to various states.

In one embodiment, step 209 may include generating an anatomic model of the second state, based on flow and pressure conditions of the patient in a second state. In one embodiment, step 209 may include updating and/or revising a patient-specific first-state model (e.g., the patient-specific anatomic model from step 201). For example, step 209 may include simulating blood flow and pressure of the patient in the second state, using the patient-specific anatomic model and biomechanical model of the patient in the first state. In other words, step 209 may include simulating blood flow and pressure in the first-state model, along with boundary conditions and/or material properties associated with the second-state model. Further detail regarding step 209 is provided in FIGS. 3 and 4.

In one embodiment, step 211 may include performing simulations using a model reflecting a patient's second state. For example, step 211 may include performing a simulation of blood flow and pressure using the second-state model. Furthermore, step 213 may include providing and/or outputting results of the simulation in the form of a report via a computer output device.

Figure 3:
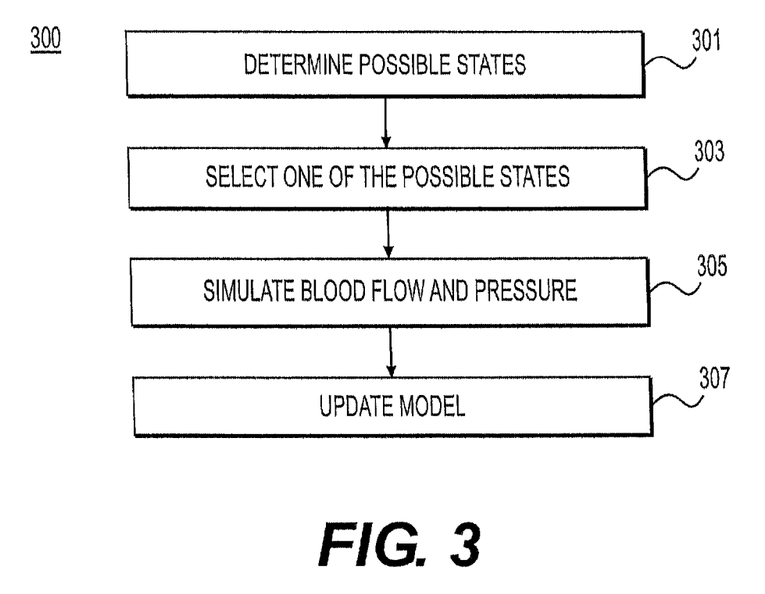
FIG. 3 is a block diagram of an exemplary method of determining a second state model of conditions, according to an exemplary embodiment of the present disclosure.

FIG. 3 is a block diagram of an exemplary method 300 of determining a second-state model of conditions, according to an exemplary embodiment. In one embodiment, step 301 may include determining various available models and/or patient conditions. For example, a second-state model may include (i) an original baseline or resting state of blood vessels (e.g., arteries) prior to administration of drugs (e.g., to improve image data), (ii) a hyperemic state subsequent to administration of a drug to increase blood flow (e.g., adenosine, papaverine, ATP, Regadenoson, etc.), (iii) a simulated exercise state, (iv) a post-treatment state, etc. In one embodiment, step 303 may include determining which of the available models is of interest. For example, step 303 may include selecting one or more of the available models as a second-state model based on user selection, inferences from input associated with the first-state model, patient information, etc.

In one embodiment, step 305 may include determining conditions associated with the selected model. For example, in response to a hyperemic state, physiologic condition changes may include: aortic pressure decreases, heart rate increases, vascular microcirculatory resistance decreases, healthy arteries dilating in response to flow, stenosis or segments of arteries downstream of disease reducing in size in response to pressure changes, etc. In another example, a response to a simulated exercise state may include the following physiologic condition changes: cardiac output increases, aortic pressure increases, heart rate increases, vascular microcirculatory resistance decreases, healthy arteries' dilation in response to flow, stenosis or segments of arteries downstream of disease reducing in size in response to pressure changes, etc. For a post-treatment state, for example subsequent to treatment including angioplasty and stenting or bypass surgery, local blood pressure and flow along an arterial tree may be altered for resting conditions and high flow conditions (e.g., hyperemia, exercise, etc.).

In one embodiment, step 307 may include computing forces on blood vessel walls for the second state. For example, step 307 may include simulating blood flow and pressure in the first-state model and using results of the simulation to modify physiologic boundary conditions to represent those of the second state. In one embodiment, step 307 may be performed using, for example, (i) a reduced order model (e.g., a lumped-parameter or one-dimensional wave propagation model), (ii) a three-dimensional finite element, finite volume, lattice Boltzman, level set, immersed boundary, or particle-based method to solve 3-D equations of blood flow and pressure, or (iii) a fluid-structure interaction method to solve for blood flow, pressure, and vessel wall motion.

Figure 4:
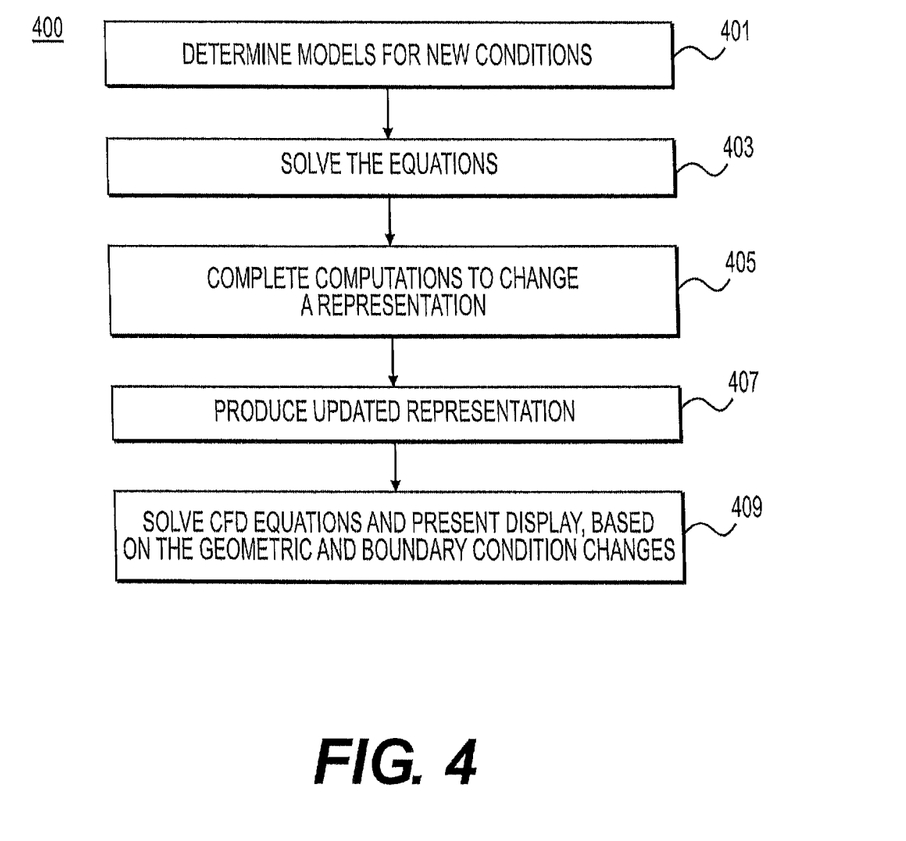
FIG. 4 is a block diagram of an exemplary method of determining an updated geometric model based on the second state conditions, according to an exemplary embodiment of the present disclosure.

FIG. 4 is a block diagram of an exemplary method 400 of determining an updated geometric model based on the second-state conditions, according to an exemplary embodiment. In other words, method 400 may be directed at determining a geometric model based on a biomechanical model of a patient's arteries (e.g., a model from method 300). In one embodiment, step 401 may include determining a relationship between geometry and biomechanical properties. For example, step 401 may include determining one or more one-dimensional elastic and/or viscoelastic models of blood vessels relating pressure to vessel cross-sectional area along the length of a vessel. In such a case, a representative pressure diameter curve may be calibrated to match pre-treatment pressure-diameter values at different centerline points. Then, a new lumen diameter may be estimated by probing the diameter of the calibrated curve at the new pressure. Alternatively, step 401 may include solving stress-equilibrium equations for a computational model of the vessel wall, with the pressure difference between the first state and the second state acting in the inner wall and a zero traction boundary condition acting on the outer surface of the vessel.

In one embodiment, step 403 may include solving the models and/or equations from step 401 to determine geometry based on the biomechanical data. For example, step 403 may include solving for geometry correction iteratively along with computational fluid dynamics (CFD) (e.g., using predictor-corrector methods). Such a method of determining the geometry may be possible because changes in geometry affect flow rate and blood pressure. Alternatively, geometry may be solved for in a coupled manner using an arbitrary Lagrangian-Eulerian framework. In another example, if experimental data relating changes in geometry to different physiologic conditions is available, machine learning methods may be used to model how cross-sectional area of vessels change locally, given a change in pressure and surrounding geometry. In some cases, training data from other patients may be used to inform the model to predict area changes from pressures computed in method 300.

In one embodiment, step 405 may include determining a deformation that may be computed to update the geometrical model. For example, step 405 may include determining a minimal deformation that creates a segmentation with desired cross-sectional area at each location, that may then be computed to update a geometry. For example, the flow domain and vessel walls may be represented by an explicit mesh. This explicit mesh may be modified by a variety of elastic deformation techniques. Alternatively, a flow domain may have an implicit representation deformed by a speed function using a level set method. A level set method may permit tracking shapes by building a surface from two-dimensional boundaries of shapes, where the shapes may include level "slices" of the surface. For example, a speed function may be used to change a representation for a level set method defined by computed desired cross sectional areas along the centerline. The speed function for a level set method may include terms to control the curvature of the implicit surface as it is modified from the first state to the second state. Step 407 may include producing a patient-specific anatomic model to represent a patient in second state conditions. Producing the second-state model may include updating a first-state geometric model. For example, step 407 may include deforming an implicit representation. Step 407 may further include determining whether to mesh the implicit representation with other representations or use the implicit representation directly. Step 409 may include using either a mesh of multiple implicit representations or a single implicit representation of modified boundary conditions for display, calculations of CFD equations, or a combination thereof. For example, step 409 may include performing a simulation of blood flow and pressure using the second-state patient-specific anatomic model and/or biomechanical model. In a further example, step 409 may include providing information based on the simulation to a user, for instance, through a report or display via a computer output device.

In one embodiment, method 400 may include further modeling geometric changes based on post-treatment states (e.g., angioplasty, stenting, or bypass surgery). For example, deforming the mesh for an anatomic model in step 407 may include accounting for a geometry of a stent or a geometry post-angioplasty. Then, a simulation of step 409 may include simulating blood flow and pressure through the anatomic models built from physiologic state boundary conditions and geometry, as well as treatment-related geometry. As a further step, results from the simulations may be output or displayed. For example, such output may include a treatment recommendation, where several simulations may be run to simulate various treatment options.

FIG. 5 is a block diagram of an exemplary method 500, such as machine learning methods, of determining geometry responses to different physiologic conditions, according to an exemplary embodiment. In one embodiment, step 501 may include determining information of a population of patients (e.g., patient age, gender, physical conditions, height, weight, diet, family medical history, etc.). Step 503 may include determining image and/or experimental data associated with the population of patients. For example, the image and/or experimental data may characterize the population of patients as a group. Alternately, image and/or experimental data may include data respective to each patient in the population of patients.

In one embodiment, step 505 may include determining or calculating a value of interest associated with the image and/or experimental data. For example, a value of interest may be a measurement (e.g., material properties of a vessel wall) and/or a change in a measurement (e.g., changes in vessel size due to administration of a nitrate). In any case, step 505 may include computing, for each patient in a population of patients, the value of interest. Step 505 may further include averaging the values for an entire population of patients. Step 507 may then include predicting a change in geometry based on the values given by the population of patients. For example, step 507 may include using the values from step 505 to model how cross-sectional area of a vessel changes locally, given change in pressure and surrounding geometry. Step 507 may then help predict area changes from pressures computed by biomechanical modeling based on physiologic conditions.

Various embodiments of the present disclosure relate to medical modeling and related methods, specifically, modeling changes in patient-specific anatomic models. For example, the present disclosure includes calculating blood flow and pressure in patient-specific arterial models updated to reflect geometric and boundary condition changes. In some embodiments, the changes arise from a state change subsequent a state of a patient in which imaging was performed. Some instances of applications for such modeling include (i) resting, exercise, or hyperemic conditions using image data obtained subsequent administration of nitrates and/or beta blockers and/or (ii) post-treatment conditions using image data obtained prior to treatment. The present disclosure describes the systems and methods directed to coronary arteries, but the disclosure may also apply to simulations of blood flow and pressure in any arterial tree including but not limited to the carotid, cerebral, renal, and lower extremity arteries.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of anatomical modeling, the method comprising:
receiving image data of one or more blood vessels of a patient's anatomy obtained while the patient's body is at a first physiological state;
determining, using a processor, a patient-specific anatomic model of the one or more blood vessels from the image data obtained while the patient's body is at the first physiological state;
determining, using a processor, a patient-specific biomechanical model of the one or more blood vessels from the image data obtained while the patient's body is at the first physiological state;
determining a second physiological state of the patient's body different from the first physiological state, wherein the second physiological state includes a hyperemic state, an exercise state, or a medicated state;
performing one or more updates to the biomechanical model using parameters associated with the second physiologic state of the patient's body;
updating the anatomic model to incorporate a geometric change associated with the parameter associated with the second physiologic state of the patient's body and at least one of the updates to the biomechanical model;
determining a treatment for modifying the patient's anatomy; and
modifying the updated anatomic model to incorporate a geometric change associated with the treatment for modifying the patient's anatomy.

2. The method of claim 1, wherein the treatment for modifying the patient's body includes angioplasty, stenting, or bypass surgery.

3. The method of claim 2, wherein the geometric change associated with the treatment for modifying the patient's anatomy includes geometry associated with the angioplasty, the stenting, or the bypass surgery.

4. The method of claim 1, wherein updating the anatomic model further includes:
determining a vessel cross-sectional area using pressure associated with the second physiological state.

5. The method of claim 1, further comprising:
receiving patient information; and
predicting the cross-sectional area using the patient information.

6. The method of claim 5, wherein the patient information includes a local change to a cross-sectional area of a vessel in response to a change in pressure or surrounding geometry.

7. The method of claim 1, further comprising:
performing a simulation using the updated anatomic model or the modified updated model; and
providing a treatment recommendation using the simulation.

8. The method of claim 1, further comprising: displaying the updated anatomic model or the modified updated anatomic model.

9. The method of claim 1, wherein updating the anatomic model includes determining a second patient-specific anatomic model.

10. A system for anatomical modeling, the system comprising:
a data storage device storing instructions for anatomical modeling; and
a processor configured to execute the instructions to perform a method including:
receiving image data of one or more blood vessels of a patient's anatomy obtained while the patient's body is at a first physiological state;
determining, using a processor, a patient-specific anatomic model of one or more blood vessels from the image data obtained while the patient's body is at the first physiological state;

determining, using a processor, a patient-specific biomechanical model of the one or more blood vessels from the image data obtained while the patient's body is at the first physiological state;

determining a second physiological state of the patient's body different from the first physiological state, wherein the second physiological state includes a hyperemic state, an exercise state, or a medicated state;

performing one or more updates to the biomechanical model using parameters associated with the second physiologic state of the patient's body;

updating the anatomic model to incorporate a geometric change associated with the parameter associated with the second physiologic state of the patient's body and at least one of the updates to the biomechanical model;

determining a treatment for modifying the patient's anatomy; and modifying the updated anatomic model to incorporate a geometric change associated with the treatment for modifying the patient's anatomy.

11. The system of claim 10, wherein the treatment for modifying the patient's body includes medical therapy, including angioplasty, stenting, or bypass surgery.

12. The system of claim 11, wherein the geometric change associated with the treatment for modifying the patient's anatomy includes geometry associated with the angioplasty, the stenting, or the bypass surgery.

13. The system of claim 10, wherein updating the anatomic model further includes:
determining a vessel cross-sectional area using pressure associated with the second physiological state.

14. The system of claim 13, wherein the system is further configured for:
receiving patient information; and
predicting the cross-sectional area using the patient information.

15. The system of claim 14, wherein the patient information includes a local change to a cross-sectional area of a vessel in response to a change in pressure or surrounding geometry.

16. The system of claim 10, wherein the system is further configured for:
performing a simulation based on the updated anatomic model or the modified updated model; and
providing a treatment recommendation using the simulation.

17. The system of claim 10, wherein the system is further configured for:
displaying the updated anatomic model or the modified updated model.

18. The system of claim 10, wherein updating the anatomic model includes determining a second patient-specific anatomic model.

19. A non-transitory computer readable medium for use on a computer system containing computer-executable programming instructions for performing a method of anatomical modeling, the method comprising:
receiving image data of one or more blood vessels of a patient's anatomy obtained while the patient's body is at a first physiological state;
determining, using a processor, a patient-specific anatomic model of one or more blood vessels from the image data obtained while the patient's body is at the first physiological state;

determining, using a processor, a patient-specific biomechanical model of the one or more blood vessels from the image data obtained while the patient's body is at the first physiological state;

determining a second physiological state of the patient's body different from the first physiological state, wherein the second physiological state includes a hyperemic state, an exercise state, or a medicated state;

performing one or more updates to the biomechanical model using parameters associated with the second physiologic state of the patient's body;

updating the anatomic model to incorporate a geometric change associated with the parameter associated with the second physiologic state of the patient's body and at least one of the updates to the biomechanical model;

determining a treatment for modifying the patient's anatomy; and modifying the updated anatomic model to incorporate a geometric change associated with the treatment for modifying the patient's anatomy.

20. The non-transitory computer readable medium of claim 19, wherein the treatment for modifying the patient's body includes angioplasty, stenting, or bypass surgery.

21. The non-transitory computer readable medium of claim 20, wherein the geometric change associated with the treatment for modifying the patient's anatomy includes geometry associated with the angioplasty, the stenting, or the bypass surgery.

22. The non-transitory computer readable medium of claim 19, wherein updating the anatomic model further comprises:
determining a vessel cross-sectional area using pressure associated with the second physiological state.

23. The non-transitory computer readable medium of claim 19, wherein updating anatomic model includes determining a second patient-specific anatomic model.

24. A computer-implemented method of anatomical modeling, the method comprising:
receiving image data of one or more blood vessels of a patient's anatomy obtained while the patient's body is at a first physiological state, wherein the first physiological state includes a hyperemic state, an exercise state, or a medicated state;

determining, using a processor, a patient-specific anatomic model of one or more blood vessels from the image data obtained while the patient's body is at the first physiological state;

determining, using a processor, a patient-specific biomechanical model of the one or more blood vessels from the image data obtained while the patient's body is at the first physiological state;

determining a second physiological state of the patient's body different from the first physiological state;

performing one or more updates to the biomechanical model using parameters associated with the second physiologic state of the patient's body;

updating the anatomic model to incorporate a geometric change associated with the parameter associated with the second physiologic state of the patient's body and at least one of the updates to the biomechanical model;

determining a treatment for modifying the patient's anatomy; and modifying the updated anatomic model to incorporate a geometric change associated with the treatment for modifying the patient's anatomy.

* * * * *